United States Patent [19]

Zelmanovic et al.

[11] Patent Number: 4,677,298

[45] Date of Patent: Jun. 30, 1987

[54] METHOD OF MONITORING INK-WATER BALANCE ON A LITHOGRAPHIC PRINTING PRESS

[75] Inventors: David Zelmanovic, Monsey; Stanley J. Kishner, Pomona, both of N.Y.

[73] Assignee: Kollmorgen Technologies Corporation, Dallas, Tex.

[21] Appl. No.: 618,252

[22] Filed: Jun. 7, 1984

Related U.S. Application Data

[63] Continuation-in-part of Ser. No. 560,837, Dec. 13, 1983, abandoned.

[51] Int. Cl.⁴ .................. G01N 21/49; G01N 21/55
[52] U.S. Cl. .................. 250/341; 101/DIG. 24; 250/358.1; 356/446
[58] Field of Search ............... 101/148, 350, DIG. 24; 250/339, 341, 358.1, 359.1, 573, 574; 356/445, 446, 447, 448; 427/10

[56] References Cited

U.S. PATENT DOCUMENTS

| | | | |
|---|---|---|---|
| 3,065,665 | 11/1962 | Akhtar et al. | 356/446 |
| 3,177,757 | 4/1965 | Polanyi | 250/574 |
| 3,439,175 | 4/1969 | Kammuller et al. | 101/148 |
| 3,693,025 | 9/1972 | Brunton | 356/446 |
| 3,870,884 | 3/1975 | Williams | 250/359.1 |
| 3,960,451 | 6/1976 | Wirz et al. | 250/573 |
| 3,999,864 | 12/1976 | Mutter | 356/448 |
| 4,707,197 | 10/1983 | Jeschke | |

FOREIGN PATENT DOCUMENTS 3134264 3/1983 Fed. Rep. of Germany ... 101/DIG. 24

Primary Examiner—F. L. Evans
Attorney, Agent, or Firm—Morgan & Finnegan

[57] ABSTRACT

In a lithographic printing system, a light source and a plurality of photodetectors are used to monitor the amount of fountain solution interacting with the ink. The light source irradiates an ink form roller and the photodetectors are disposed at a specular angle and at one or more non-specular angles to monitor the reflected light. An electronic circuit is responsive to the output of the photodetectors and is used for providing an indication of the amount of fountain solution emulsified in the ink, and lying on the surface of the ink.

63 Claims, 5 Drawing Figures

METHOD OF MONITORING INK-WATER BALANCE ON A LITHOGRAPHIC PRINTING PRESS

This application is a continuation-in-part of U.S. patent application Ser. No. 560,837 filed Dec. 13, 1983, now abandoned.

BACKGROUND OF THE INVENTION

1. Field of the Invention

Lithography is a widely used process in the field of commercial printing, for the production of such items as newspapers, magazines, advertising brochures and packaging materials. The quality of printing, primarily four-color printing, has steadily improved due to advances in the quality of inks, papers and printing machinery. In addition to improved mechanical designs in printing presses, automatic means of monitoring and controlling various aspects of press operation have contributed to improved printing quality.

Offset lithographic printing involves the transfer of ink via a set of rollers to image areas of a printing plate, which are oleophilic. From these image areas, ink is transferred to a rubber cylinder called a blanket, which then applies the ink to paper or other substrates. In addition to ink, a hydrophilic fountain solution, composed mainly of water, is applied via a set of rollers to the hydrophilic non-image areas of the printing plate. The fountain solution keeps the ink from covering the non-image area. In addition to water, the fountain solution often contains iso-propanol or surfactants similar in composition to soap, as well as other possible ingredients. Fountain solution is often referred to simply as "water".

It should not be assumed from the previous statements that the fountain solution and ink do not mix, or even that their mixing is undesirable. In fact, practical experience shows that proper printing requires that some fountain solution be emulsified in the ink. If too little fountain solution is in the ink, the ink can spread into the non-image areas. This is called plate "catch-up. In addition, too little water can increase ink tack, causing "picking", a removal of part of the surface of the printed page. Thus, a proper "ink-water balance" is desired.

Emulsification of ink in water is caused by the extremely high pressure in the nip between the ink form roller, which is coated with ink, and the lithographic plate, which is coated with fountain solution in the nonimage areas prior to contact with the ink roller. In Dahlgren dampening systems, fountain solution is applied directly to the ink form roller. Further emulsification arises in the form roller-distributor nip.

The degree of emulsification of the fountain solution in ink is a function of the fountain solution itself, the particular ink, press roller speed, number of rollers, pressure between rollers, ambient temperature, humidity and numerous other variables. Also, it is necessary to distinguish between the total fountain solution in contact with ink and that actually emulsified in ink. Fountain solution located on the surface of the ink does not alter the rheological properties of the ink as does emulsified solution. As the printing press runs, many of the variables described above will change, causing the interaction between ink and water to change.

2. Description of the Prior Art

An automatic instrumental method of monitoring the fountain solution and its interaction with ink is desirable in light of the importance of proper ink-water balance. Prior attempts to monitor ink-water balance include D. L. Southam's (U.S. Pat. No. 3,499,383) and P. R. Kantor's (U.S. Pat. No. 3,412,677) determination off fountain solution level by electrical conduction measurements or D. K. Mikan and A. A. Presti's (U.S. Pat. No. 3,822,643) determination by impedance measurements on water layers in roller nips using auxiliary rollers. A related approach by W. E. Dauterman (U.S. Pat. No. 3,730,086) measures the capacitance of a layer of fountain solution between an auxiliary roller and a concentric capacitor plate. These methods require modification of the press, determine the amount of fountain solution only and do not distinguish between surface and emulsified solution. The use of gloss measurements on the printing plate, as described by J. Albrecht, W. Rebner and B. Wirz (Forschungsbericht Land Nordheim Westfalen No. 1523 Westdeutscher Verlag, Cologne, 1966) or the use of infra-red absorption measurements of water on the printing plate, as described by B. Wirz, R. Bosse, P. Decker and D. Pyliotis (Fogra Institutsmitteilung 3202/3203, Munich 1972) are used to determine only the amount of fountain solution in the former case and water in the latter. Neither method determines both surface and emulsified solution. Both techniques require changes in the position of the light source and detector to accomodate the position of the non-image areas, which will differ from plate to plate. Reflectance measurements with the plate as a substrate are subject to interference patterns arising from thin oxide layers on the plate, and can vary as the plate wears. Interference fringes also arise due to the thinness of the layer of solution on the plate (typically<5 micrometers). Furthermore, the position and intensity of the absorbance peak due to the hydroxyl group in water is subject to the nature and concentration of the fountain solution additives. S. Karttunen and M. Ilvessuo (NATS Research Report, Graphic Arts Research Institute, Otaniemi, 1975) and K. Reich (Research Report, IGT Leipzig, 1964) describe a method of gravimetrically determining the amount of water, off line, and without distinguishing surface and emulsified water. Karl Fischer titration for determination of amount of water or T. Saynevirta and S. Karttunen's (Graphic Arts in Finland 2 (1973) 2, pp. 1–12) method of doping the solution with a radioactive tracer to determine the amount of solution both determine only water or solution content, do not distinguish between surface and emulsified water and are each off-line methods. D. Pyliotis's approach of taking infra-red measurements of the ink and water using an auxiliary roller (Fogra Forschungsberich No. 5 205, 1978) and J. Albrecht and M. Heigl's technique of measuring the change in dielectric constant of ink as a function of added solution (Fogra Mitteilungen 14 (1965), 47, pp. 3–9) require modification of the press and do not distinguish between surface and emulsified solution. G. W. Jorgensen's (U.S. Pat. No. 3,191,528) approach of attaching a tackmeter to an ink roller and measuring ink tack, requires contact between the meter and the roller and, of course, measures only tack.

SUMMARY OF THE INVENTION

It has beenfound that by measuring light reflected at one or more angles from an ink form roller on a printing press, one can obtain information about the amount of surface fountain solution, as well as the amount of emulsified solution. Furthermore, it has been found that the relative amounts of emulsified and surface fountain solution are different for areas of the ink form roller that have previously contacted image and nonimage areas of the printing plate. Measurement of emulsified and surface fountain solution, then, in areas of the ink form roller corresponding to image and nonimage areas of the printing plate can be used to control the dampening system to maintain proper ink-water balance. The measurement can be conducted on-line, is noncontact, does not require modification of the press, and since a wavelength of light is chosen so that it is not significantly absorbed by any of the media with which it interacts, the technique is applicable without modification to a wide variety of fountain solutions, inks and substrates. The technique is also applicable to the measurement of emulsions other than those used in printing, including water-in-oil and oil-in-water emulsions.

It is therefore an object of this invention to measure the amount of dampening solution present on an ink form roller of an offset printing press.

It is a further object of this invention to measure, separately, the amount of emulsified and surface fountain solution in ink with an on-press sensor, during operation of the press.

It is a further object of this invention to measure the amount of emulsified and surface fountain solution in areas of an ink form roller that correspond, separately, to image and nonimage areas of the printing plate.

It is a further object to provide a measurement of fountain solution in ink without the use of an auxiliary roller.

It is a still further object to provide a measurement of fountain solution in ink that is applicable to a wide variety of fountain solutions and inks without modification of the sensor.

It is a still further object of this invention to measure the amount of fountain solution emulsified in and lying on the ink on an ink form roller, for the purpose of controlling the ink-water balance on a lithographic printing press.

It is a still further object to provide a measurement of the amount of hydrophilic substance emulsified in an oleophilic substance, or the amount of an oleophilic substance emulsified in a hydrophilic substance.

DETAILED DESCRIPTION OF THE INVENTION

Figure 1:
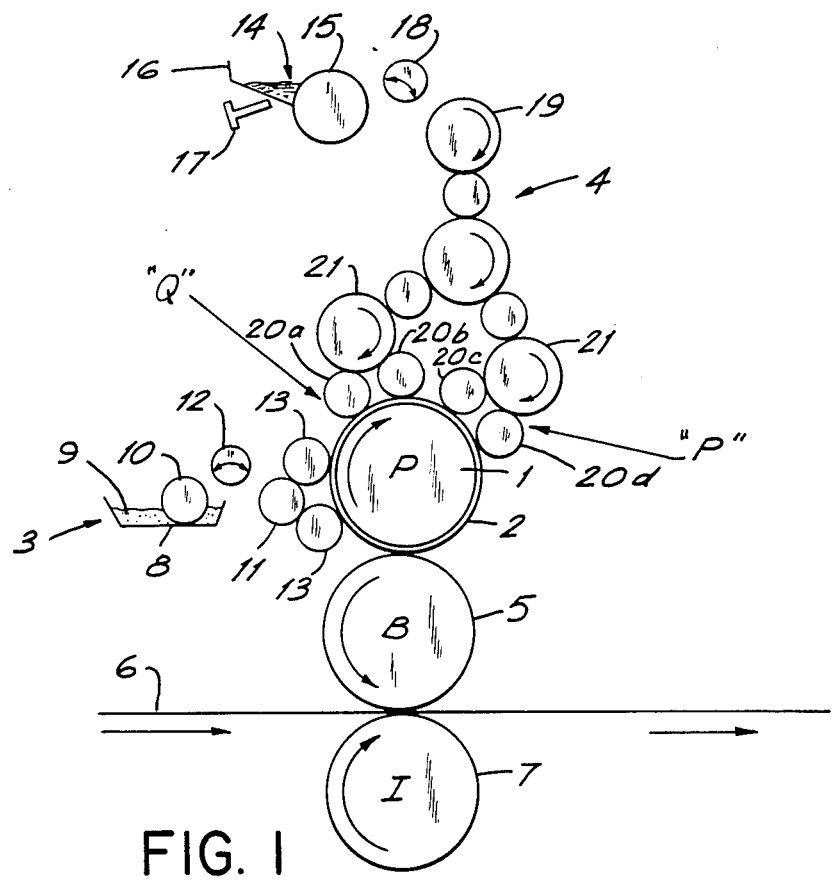
FIG. 1 depicts dampening and inking systems on a lithographic press, and indicates two possible locations for mounting the ink-water sensor.

Since it is an object of the invention to monitor the interaction between ink and water, it is necessary to properly position the sensor on the press. It is therefore instructive to describe, first, the operation of the dampening and inking systems on a lithographic press. FIG. 1 depicts typical dampening and inking systems on a lithographic press. The plate cylinder 1, on which the printing plate 2 is mounted, first makes contact with the dampening system 3, and then the inking system 4. The ink on the plate 2 is then transferred to the blanket-cylinder 5. The blanket 5 then transfers the inked image to the paper 6. The impression cylinder 7 serves as a backing for the paper 6 at the printing nip.

The dampening system 3 begins at the water fountain 8, commonly called the pan, which contains the dampening solution 9. Dampening solution 9 is then transferred from the fountain roller 10 to the distributor roller 11 by means of the ductor roller 12, which oscillates back and forth alternately contacting the fountain and distributor rollers 10 and 11. The form rollers 13 transfer the dampening solution to the plate 2. It should be noted that although the dampening system depicted in FIG. 1 is the most common system used, there are various other configurations that yield the same result—the application of dampening solution to the nonimage areas of the printing plate 2. In any of the dampening systems, there is a means for controlling the flow of dampening solution. For example, the speed of rotation of the fountain roller 10 will vary the flow of dampening solution to the ductor 12.

The inking system begins at the ink fountain 14. Ink is metered onto the fountain roller 15 by means of a fountain blade 16. The physical separation between the fountain blade 16 and the fountain roller 15 is controlled by a series of ink keys 17 disposed at equal spacings accross the width of the press, along the fountain blade 16. These ink keys 17 are used to control the flow of ink independently to different positions across the width of the web 6. The flow of ink from the fountain roller 15 to the rest of the inking chain is controlled by the ductor roller 18, which oscillates back and forth between the fountain roller 15 and the first distributor roller 19. From this point on, ink is distributed through a series of rollers, the purpose of which is to provide an even flow of ink of proper thickness. As depicted in FIG. 1, four ink form rollers 20a, 20b, 20c and 20d contact the plate. It should be noted that there are various other inking system designs that achieve the same function.

Let us now track a point on the surface of the printing plate as the plate cylinder rotates. This point first contacts the dampener form rollers 13. If it is an image point, it is hydrophobic, and will have little or no water transferred to it. If it is a nonimage point, it is hydrophilic, and will accept a film of water. The point next contacts, in sequence, the ink form rollers 20a, 20b, 20c and 20d. If it is an image point, ink is transferred to it. If it is a nonimage point, it will not accept ink from the ink form rollers 20a, 20b, 20c, 20d. However, it will transfer some of its water film to the ink form rollers 20a, 20b, 20c, 20d. In fact, this is the primary mechanism for transfer of water to the ink. Once transferred, the water may reside in the ink (See, for example, S. Karttunen and V. Lindquist, "Interfacial Phenomena in Litho Offset Printing, Part I, "Graphic Arts in Finland, No. 2, 1978, p. 10) as emulsified droplets, or as a layer on the surface of the ink.

As is evident from the above discussion, the plate-ink form roller nip is the primary source of ink-water interaction. Therefore, ink-water balance must be measured either on the plate 2 or on the ink form rollers 20a, 20b, 20c, 20d. Measurement on the plate 2 present numerous difficulties. First, in attempting to measure nonimage areas of the plate 2 it is necessary to realize that metal plates 2 are generally covered with a thin oxide layer, which may cause the appearance of an interference pattern in the reflected beam. Second, the thin layer of water present may also cause interference. These interference patterns modulate the intensity of the reflected beam in an unpredictable way, rendering the data less reliable than in the absence of these patterns. When measuring the image areas it is important to note that while they are covered with ink as are the ink form rollers 20a, 20b, 20c, 20d, the ink on the plate 2 will not carry a significant surface film of water. It is thus impossible to determine directly, by measurements on the plate 2, the fraction of water on the surface of the ink. In light of these difficulties, it is preferrable to measure the ink-water balance on an ink form rollers 20a, 20b, 20c, 20d.

Let us consider the behavior of a point on any of the ink form rollers 20a, 20b, 20c, 20d immediately after having contacted the plate 2. Since, in conventional dampening systems, the first ink form roller 20a has more water transferred to it than any of the others, it is preferable to measure the ink-water interaction of a point on this roller just following the plate-ink form roller nip. However, this point and the corresponding points on form rollers 20b and 20c are normally inaccessible. Therefore, it becomes necessary to measure at point "P" on the last ink form roller 20d, as indicated by FIG. 1.

In the image areas, the ink on the form rollers 20a, 20b, 20c, 20d and the ink on the plate 2 meet at the plate—orm roller nip and the contacted layers undergo a split, wherein ink from the form roller is transferred to the plate, and a small portion from the plate is transferred to the form roller. Although this nip does not serve to significantly change the composition of the ink on the form rollers 20a, 20b, 20c, 20d, the ink-water emulsion on the ink form roller is representative of that which is transferred to the blanket 5, and then printed. This emulsion may be optically characterized by its reflectance properties. Since it is an emulsion, it will diffusely scatter incident light. In fact, visual examination of the surface of the ink form rollers 20a, 20b, 20c, 20d immediately after contacting the plate 2 through the use of a stroboscope (not shown) that is triggered once per rotation of the plate cylinder 1, reveals at image areas are matte in appearance. Therefore, they may be characterized by measuring the intensity of diffusely reflected light.

In the nonimage area—form roller nip, surface water on the plate 2 is transferred to the ink form rollers 20a, 20b, 20c, 20d. Visual examination under stroboscopic illumination reveals a glossy appearance. This gloss may be characterized optically by measuring the intensity of specularly reflected light. This gloss is a result of the smooth film of water lying on the surface of the ink, having been transferred from the plate 2.

Let us now consider the behavior of a point on the ink form roller 21a immediately following contact with an ink distributor roller 21. Such a point is designated "Q" in FIG. 1. The distributor rollers 21 serve two purposes. First, they provide a fresh supply of ink to the form rollers 20a, 20b, 20c, 20d. Second, they oscillate laterally, thereby distributing the ink evenly. This new supply of ink obscures the previously applied films, thereby diminishing the distinction between image and nonimage areas. Additionally, the oscillatory motion of the distributor rollers 21 mixes laterally adjacent image and nonimage areas, further diminishing the distinction between image and nonimage areas. Therefore, measurement at this point is not preferred, since it yields less information than can be obtained by measuring image and nonimage areas at point "P".

The major difference between a conventional (direct) and an indirect dampening system is that in the former, fountain solution is applied directy to the plate 2 while in the latter it is applied to the first ink form roller 20a.

Figure 2:
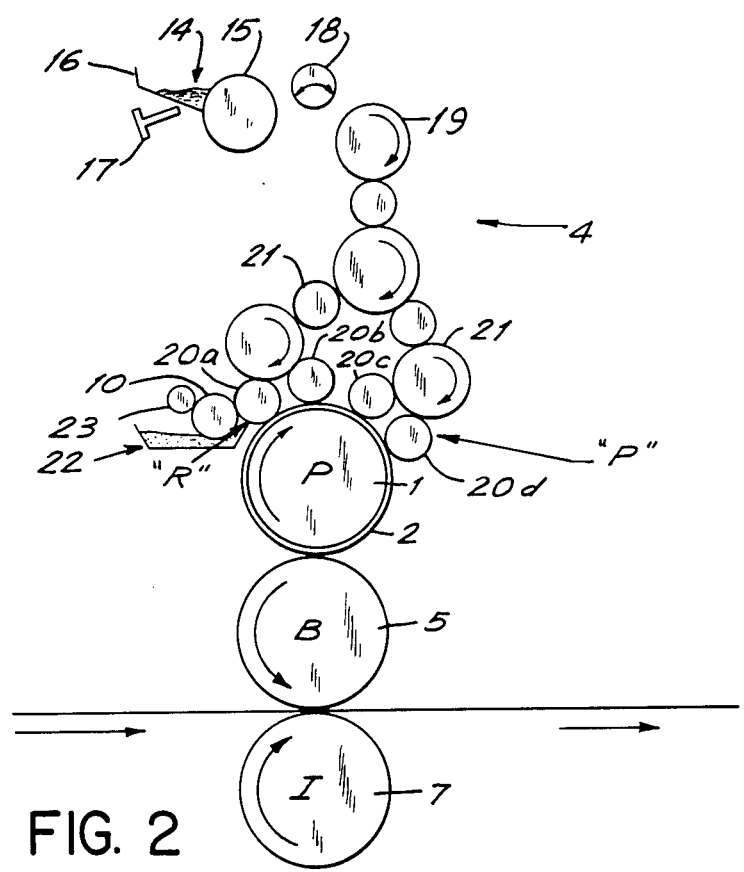
FIG. 2 is similar to FIG. 1, but shows an indirect dampening system rather than a direct dampening system.

FIG. 2 shows the use of an indirect dampening system 22 on a lithographic press. The dampening fountain roller 10 now contacts the first ink form roller 20a directly. Metering roller 23 controls the thickness of the film of water that is transferred. The state of the first ink form roller 20a immediately after contacting the plate 2 will be very different in the case of indirect dampening, since it is now a source of water as well as of ink. The first ink form roller 20a now carriers an emulsion. When in contact with an image area, the emulsion is transferred as a unit (water included) to the plate 2. Therefore the composition of the ink on the form roller 20a does not change radically in the image area-ink form roller nip. When in contact with a nonimage area, however, the form roller 20a tranfers only water to the plate 2 and the emulsion becomes poorer in water. This is in contrast to the situation in a conventional dampening system, wherein the plate 2 transfers water to the first ink form roller 20a in the nonimage area-ink form roller nip. Successive ink form rollers 20b, 20c, and 20d behave similarly in the two dampening systems, since only the first ink form roller 20a is dampened. The indirect dampening system offers an additional probe point of ink-water interaction. This is immediately following the fountain roller-first ink form roller 20a nip, as indicated by point "R" in FIG. 2. This point exhibits similar behavior to that at point "P" in FIG. 1 of the conventional dampening system, since it is at this point that water is transferred to the first ink form roller 20a. In the indirect dampening system, however, more water is transferred to the form roller 20a, since the system is designed to purposely transfer water to the plate 2 via the ink form roller 20a. Additionally, the system is designed to transfer the water to the form roller 20a as an emulsion. Therefore relatively little surface water is transferred to the first ink form roller 20a in this nip. Unfortunately, this point is also normally inaccessible and, therefore, measurements must be conducted at point "P" on the last form roller 20d in this dampening system as well.

Measurement of selected regions on the ink form roller 20d that correspond to image and nonimage areas of the plate 2 requires that the sensor be synchronized with the rotation of the plate cylinder 1. This synchronizatin can be achieved in a number of ways, on of which is the use of a shaft encoder on the drive shaft that controls the rotation of plate cylinder 1. The encoder provides pulses which correspond to equal angular positions of the plate cylinder 1 as it rotates. The sensor makes a measurement when the encoder provides a pulse corresponding to an image area (on the form roller) falling adjacent to the sensor, and makes a second measurement when the encoder pulse likewise corresponds to a nonimage area.

If the image and nonimage areas at which measurements are to be made can be predetermined, synchronization, once achieved, need not be adjusted. If their locations are consistent from job-to-job, then operator intervention is not necessary. Measurement without such synchronization will result in very complicated readings, because the sensor differentiates strongly between image and nonimage areas. These areas are measured at random if synchronization is not used. Analysis is possible, but quite complicated. For this reason, synchronization is preferred.

To probe to interaction between water and ink, it is desirable to measure specularly and diffusely reflected light, in both image an nonimage areas on the ink form roller. Increase in the flow of water relative to the ink will increase the amount of emulsified and surface water in both image and nonimage areas. This will result in increased diffuse reflectance corresponding to the increased emulsification, as well as increased specular reflectance corresponding to the increase in thickness of the surface water film. However, these changes are greater in nonimage areas, because a larger amount of water is transferred to the ink form roller.

If an image is to be measured, it should be a solid rather than a halftone, so that it may be as representative of the emulsification of water in ink as possible. If a solid area does not appear in the image, then a solid patch can be included in the margin or at the leading or trailing edges of the impression. Alternatively, the gap that exists between the ends of the plate 2, when mounted on the plate cylinder 1, can also be used as an image area. Since the gap does not contact either the blanket cylinder 5 or ink form roller 20a, 20b, 20c, 20d, the sensor will measure a region on the ink form roller that has been inked by the distributor roller 21.

A nonimage area can always be found along the leading or trailing edge of the impression (adjacent to the gap).

In general, a strip of arbitrary width along a printing plate 2 will contain a distribution of image and nonimage areas. Therefore, the state of the ink film on the form rollers 20a, 20b, 20c, 20d at any time will depend on the point it has just contacted. Thus, it is necessary to make the measurement of a duration short enough to avoid averaging of image and nonimage areas.

A particularly useful application of the invention is the sensing of the onset of plate catch-up. Catch-up is caused primarily by insufficient water on the nonimage areas of the plate 2. The intensity of the specular reflection from the nonimage area at point "P" (FIG. 1) will decrease rapidly at the onset of catch-up, since the film of water on the plate 2 is extremely thin.

An additional useful application is the sensing of emulsified water to determine the rheological properties of the ink. This is important in controlling dot gain. It is of further advantage to use the ink-water balance sensor in conjunction with a densitometer, which can be used to directly measure dot gain. The proper choice of ink-water balance can then be made based on simultaneous measurements of emulsified water and dot gain.

Conditions on the press cause the water-in-ink emulsion to be unstable and short-lived. It is possible to monitor the breakdown, in time, of the emulsion on a point on the ink form roller by placing two sensors in series along the circumference of the ink form roller and measuring the same point on the roller sequentially in time. This would require synchronization of the sensor with rotation of the ink form roller. Under breakdown of emulsification, the intensity of specularly reflected light will increase as water comes out of the emulsion to the surface, while the intensity of diffusely reflected light will decrease. A measurement of the difference between specular and diffuse reflectance is a useful index of the emulsion lifetime. Emulsion lifetime is important in determining ink rheology, which of course affects printing quality.

As previously discussed, the sensor can measure, independently, emulsified and surface water. These quantities are not necessary proportional to each other, and cannot both be controlled by adjusting a single parameter, such as water feed. For example, the amount of emulsified water is a function of fountain solution surface tension (as determined by surfactants and other additives), fountain solution pH, ink composition and other factors. The amount of water on the plate 2 is also affected by fountain solution surface tension and the condition of the plate 2. Therefore, it may be necessary to adjust the chemical composition of the ink and/or fountain solution, in addition to water feed, in order to adjust the amounts of both emulsified and surface water.

Figure 3:
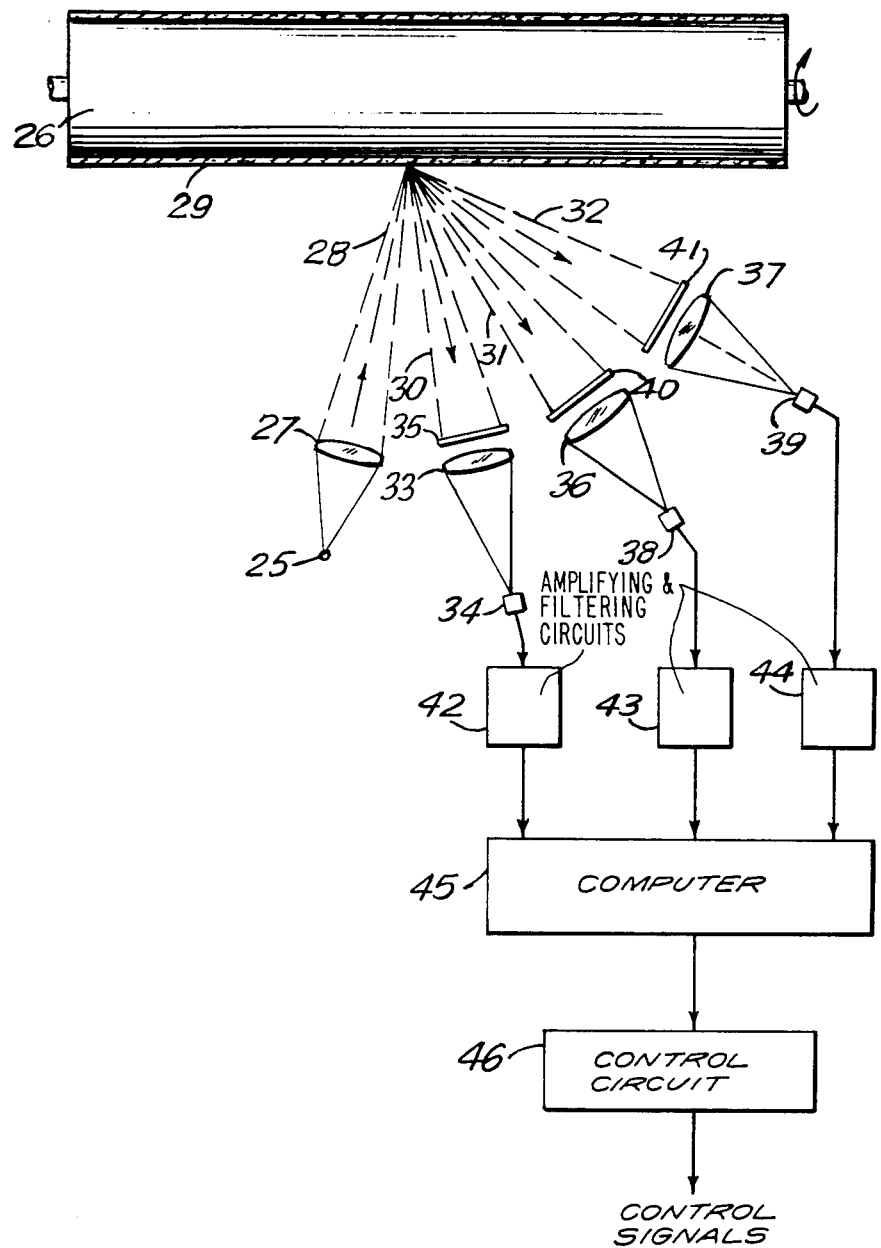
FIG. 3 is a diagram showing a generalized configuration for an optical system that can measure the specular and diffuse reflectance of an ink form roller.

FIG. 3 shows a block diagram of a generalized optical system that can be used to measure specular and diffuse reflectance. We see that a light source 25, such as an incandescent tungsten lamp, a xenon arc lamp, a laser or a light-emitting diode, is used to illuminate a spot on the ink form roller 26, via an illumination optical system, depicted as a lens 27. There are a number of possible optical configurations that can be used to provide such illumination, including systems that image the light source 25 directly on the ink form roller 26, and systems that project a uniformly illuminated aperture onto the ink form roller 26, the latter type of system commonly known as a "projection" optical system. The incident light rays depicted as dotted lines 28, interact with the water-in-ink emulsion 29 on the surface of the ink form roller 26. A portion of the light is specularly reflected, as from a mirror, by any surface water that covers the emulsion 29. These specularly reflected rays are depicted by dotted lines 30. Another portion of the incident light 28 is diffusely scattered by both pigment particles and microscopic water droplets in the emulsion 29. Yet another portion of the incident light 28 interacts with the surface of the ink form roller 26, which will reflect light both specularly and diffusely. The specularly reflected light will follow the path of the rays 30 that are specularly reflected from any surface water. Light that is diffusely reflected by the emulsion 29 as well as the surface of the roller 26 will emanate in all directions. However, we will be interested in those rays depicted as dotted lines 31 and 32.

The specularly reflected rays 30 are collected by a receiving optical system, depicted as a lens 33, and sensed by a photodetector 34. The received light passes through an optical filter 35 that isolates the desired band of wavelengths, preferably in a spectral region that is not significantly absorbed by either the ink or dampening solution. The filter 35 performs two functions. First, it passes only those wavelengths from the source 25 that lie within the desired spectral band. However, when a monochromatic source, such as a laser or light emitting diode is used, this function is unnecessary. Second, the filter 35 eliminates undesired wavelengths due to ambient light. The necessity of performing this function depends on the intensity of the collected light 30 as compared with any ambient light that is collected.

Light rays 31 and 32 represent scattered or diffusely reflected light collected at two different angles. These scattered rays 31 and 32 are collected by collection optical systems 36 and 37, and sensed by photodetectors 38 and 39. Optical filters 40 and 41, identical to optical filter 35, can be used with optical collection systems 36 and 37. Electronic circuits 42, 43 and 44 are used to provide electrical output signals corresponding to the intensity of the light sensed by photodetectors 34, 38 and 39, respectively. These electronic circuits are generally used to amplify and filter the signals generated within the photodetectors 34, 38, 39. These output signals can be of either analog or digital form. Further computer means 45 is provided for calculating the percent emulsified and percent surface water from the sensor output signals. This information can be used directly as an indicator to the printing press operator, or can be transmitted to a control circuit 46, implemented in either analog or digital fashion, such that the circuit effects direct control of the flow of dampening solution.

The choice of angles at which the diffusely reflected rays 31 and 32 are positioned relative to the specular ray 30 can affect the accuracy of the technique. In general, there is a minimum useful angular separation between rays 30, 31 and 32. For example, as the angle between rays 30 and 31 is decreased, the signals sensed by photodetectors 34 and 38 will become closer in magnitude. Furthermore, ray 31 will contain some specular reflection, and will thereby become somewhat dependent upon surface water. Additionally, if rays 31 and 32 are closely spaced in angular position, they will approach each other in magnitude, so that their ratio will approach unity, and will become independent on ink-water balance. In general, mutual angular separations between rays 30, 31 and 32 should exceed 5°.

It should be noted that the use of the specular and one diffuse angle is sufficient to monitor, separately, the amount of emulsified and surface water on the ink form roller. Additional diffuse angles, however, can be used to provide additional information which may indicate the size distribution of emulsified water droplets. The use of measurements of light scattered at various angles is an accepted technique for the analysis of particle size distributions (see, for example, H. C. Van de Hulst: "Light Scattering by Small Particles," Dover Publications, N.Y., 1981). Therefore, the inclusion of more than one diffuse angle in the ink-water sensor would make the sensor useful for research purposes, and may find practical use if knowledge of droplet size distribution proves to be a useful process parameter.

There are a number of ways in which the output signals can be used in calibrating and operating the sensor. The intensities of light rays 30, 31 and 32 are designated as;

$I_{30} = I_{D30} + I_{S30}$ $I_{31} = I_{D31}$ $I_{32} = I_{D32}$ where the subscripts D and S stand for diffuse and specular, respectively. ($I_{32}$ is not applicable when one diffuse angle is used.) Note that $I_{30}$ has a diffuse, as well as a specular component. Emulsified water is associated with the diffusely scattered rays $I_{D30}$, $I_{D31}$ and $I_{D32}$, and surface water is associated with the specular ray $I_{S30}$. Since a measurement of $I_{30}$ yields only the total intensity, $I_{D30} + I_{S30}$, it is necessary to find a method for separating these components in order to calibrate or operate the sensor, so that the relationship between $I_{D30}$, $I_{D31}$, and $I_{D32}$ and emulsified water and $I_{S30}$ and surface water may be established. Having established these relationships we will be able to monitor, separately, the changes in behavior of the surface and emulsified water during actual press runs.

One method by which the sensor can be calibrated utilizes the fact that only the specular component of ray 30 retains the polarization state of incident light ray 28. As a result, this component may be eliminated by placing a polarizer in the path of ray 28 and an analyzer (i.e., a second polarizer, whose major transmission axis is perpendicular to that of the first polarizer), in the path of ray 30. This technique may be incorporated into the calibration procedure, in order to separately observe the effects of surface and emulsified water.

The calibration procedure is as follows. With reference to FIG. 3; intensities $I_{30}$, $I_{31}$ and $I_{32}$ are measured, with polarizers in the paths of ray 28 and ray 30 as indicated above, during a press run of respective length. The ink-water balance should be varied during the press run. Since the polarizers are interposed in the indicated manner, $I_{30} = kI_{D30}$, where k is the transmittance of the analyzer. At various times during the run, values of $I_{30}$, $I_{31}$ and $I_{32}$ are recorded, and surface droplets of water are blotted off the roller 26 and the ink-water emulsion scraped off the roller. The ink-water emulsion is then chemically analyzed for percent emulsified water. The emulsified water is removed from the ink by shaking the emulsion vigorously in anhydrous methanol. The methanol solution is immediately titrated against Karl Fischer Reagent and the mass of emulsified water determined. The ink is dissolved in a suitable solvent such as carbon tetrachloride and the optical density of a sample of the solution is measured spectrophotometrically. The optical density is proportional to the mass of the ink. The optical density is divided by the proportionality constant and the result equals the mass of ink. The proportionality constant is determined by measuring the optical density of a solution of a known mass of ink in a known volume of solution and then dividing the optical density by the mass of ink per volume of solution. Intervals at which the ink-water emulsion is analyzed should be sufficiently large so that a steady value of ink-water balance is obtained. After the completion of the press run, tables of $I_{D30}$, $I_{D31}$ and $I_{D32}$ vs. percent emulsified water are compiled.

A unique relationship exists among $I_{D30}$, $I_{D31}$ and $I_{D32}$ and percent emulsified water. It has been found, for example, that $I_{D30}$, $I_{D31}$ and $I_{D32}$ each have a unique, monotonic relationship to percent emulsified water.

Calibration of $I_{S30}$ with respect to surface water is achieved by repeating the press run without the polarizers, and without first blotting the surface water off the roller 26. In other words, the ink-water system is chemically tested for total water. In analyzing the results of this second press run, $I_{D31}$ or $I_{D32}$ is used to mathematically calculate both $I_{D30}$ and the amount of emulsified water according to the compiled tables, as above. This is achieved by referring to a table of $I_{D32}$ or $I_{D31}$ vs. percent emulsified water, and using the measured values of $I_{D32}$ or $I_{D31}$, to find percent emulsified water. Then, referring to a table of $I_{D31}/I_{D30}$ or $I_{D32}/I_{D30}$ vs. percent emulsified water, we use the value of percent emulsified water, as determined above, to find the corresponding value of the ratio $I_{D31}/I_{D30}$ or $I_{D32}/I_{D30}$. Since $I_{D31}$ or $I_{D32}$ is known, the $I_{D30}$ is found by dividing $I_{D31}$ or $I_{D32}$ by the $I_{D31}/I_{D30}$ or $I_{D32}/I_{D30}$ ratio. Actual surface water is determined by subtracting the calculated mass of emulsified water from the chemically measured total mass of water. $I_{S30}$ is determined by subtracting $I_{D30}$ from $I_{30}$ ($I_{30} - I_{D30} = I_{S30}$), and then a table of $I_{S30}$ vs. surface water is compiled.

During the press operation, one mathematically calculates emulsified water from measured values of $I_{D31}$ or $I_{D32}$. Mathematically calculated values of $I_{D30}$ are subtracted from the $I_{30}$ measurement to give the values of $I_{S30}$, from which surface water is mathematically calculated. No polarizers are necessary at this point.

A similar method of calibrating and operating the sensor involves the measurement of diffusely scattered light at one angle only. This can be implemented as the measurement of either the light reflected at a single nonspecular angle or the light reflected at the specular angle in conjunction with the use of a polarizer and analyzer. The calibration procedure is similar to those described above, wherein the percentage of emulsified water is tabulated as a function of the intensity of scattered light. This method does not account for surface water.

Yet another method by which the sensor may be calibrated and operated is based on a statistical approach. Data for $I_{30}$, $I_{31}$ and $I_{32}$ are recorded during a press run, during which ink-water balance is varied. At various intervals during the run, two samples of the ink-water mixture, which generally involves a combination of surface and emulsified water, are scraped off the roller. One is blotted before scraping and analyzed for emulsified water, and the other is analyzed for total water. In this way, both emulsified and surface water are determined. Tables of $I_{30}$, $I_{31}$, $I_{32}$ vs. both emulsified and surface water are compiled in this manner. Calibration is achieved by hypothesizing the following two equations:

$$\text{emulsified water} = a_1 I_{30} + a_2 I_{31} + a_3 I_{32}$$

$$\text{surface water} = a_4 I_{30} + a_5 I_{31} + a_6 I_{32}$$

The $a_i$ are coefficients that can be determined by least squares regression techniques, as described, for example, in "Basic Scientific Subroutines", Vol. 2, F. R. Ruckdeschel, Byte/McGraw Hill, Peterborough, N.H. (1981). Once the coefficients are determined, the above equations are used during actual sensor operation to calculate, separately, emulsified and surface water from the $I_{30}$, $I_{31}$, and $I_{32}$ measurements. This technique can also be used with data taken at more nonspecular angles, if more accuracy is required. Likewise, it will work with only $I_{30}$ and $I_{31}$ (i.e., one specular and one nonspecular angle), but without the additional information provided by the additional diffuse channel.

It should be noted that since the ink/water emulsion 29 does not appreciably absorb the incident light, a portion of light passes through the emulsion, is scattered by the surface of the ink form roller 26, and passes back out through the emulsion to be measured by photodetectors 34, 38 and 39. The effect of these signals, which are not a function of degree of emulsification, is accounted for in the above-described calibration procedures.

It should also be noted that a wavelength can be chosen such that it is partially absorbed by the ink film, and does not reach the roller 26. Preferably, the collected light is confined to a spectral region in which the absorption coefficients of the ink and dampening solution are both less than 2000/cm.

It should also be noted that although simultaneous measurement of light reflected at various angles is preferred, it is also possible to move a single receiving optical system such that is acquires measurements of light reflected at two or more angles.

Figure 4:
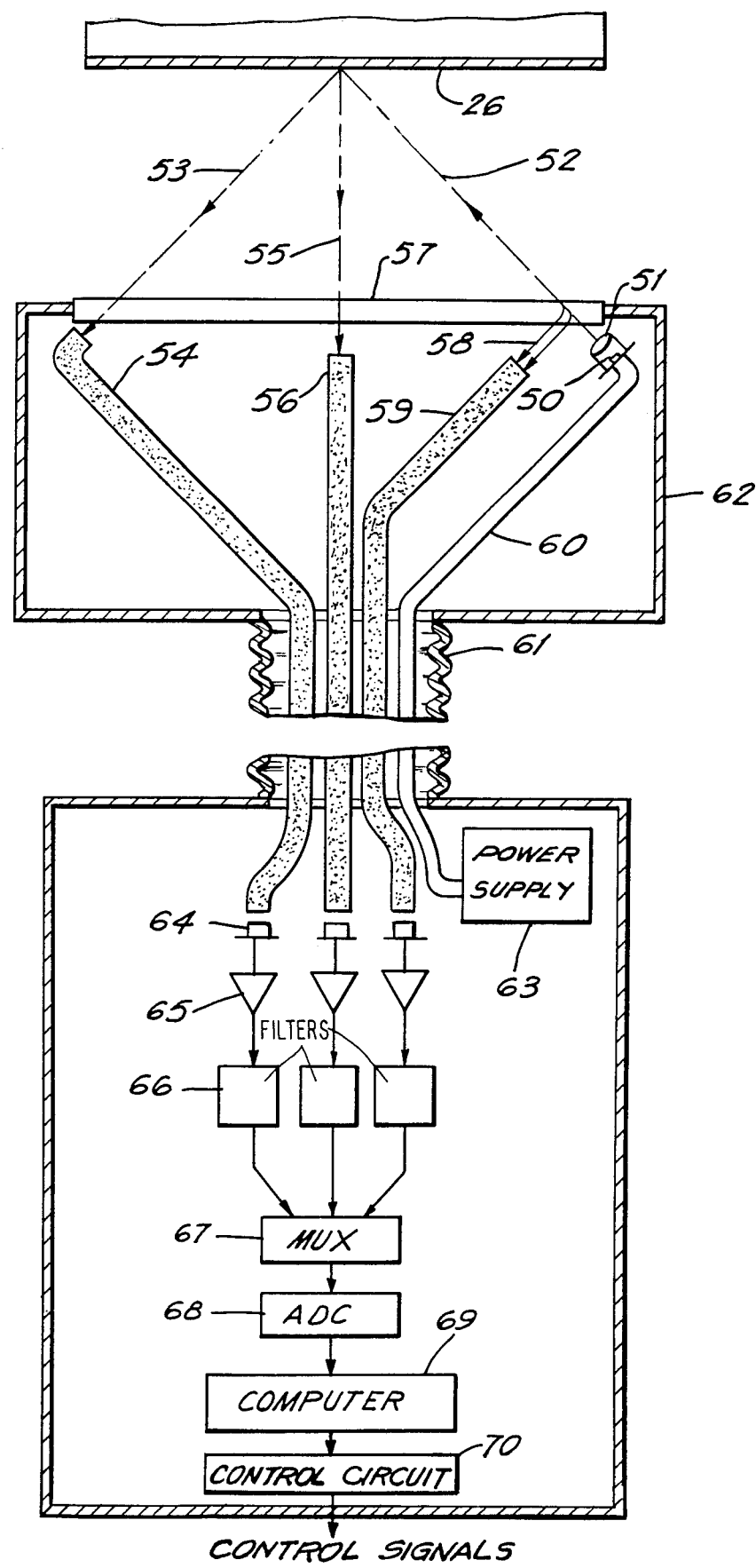
FIG. 4 shows the preferred embodiment of the invention in partial cross section.

The preferred embodiment of the sensor is shown in FIG. 4. The light source is a light-emitting diode (LED) 50, having a wavelength of 0.95 microns. At this wavelength, the absorption coefficients of the roller 26, dampening solutions and most inks is quite small. Use of this wavelength makes the sensor response relatively insensitive to the choice of these components. The LED 50 includes an integral lens 51, which reduces the divergence of the emitted beam to about 6°. The illumination beam 52 is incident on the ink form roller 26 at an angle near 45°. The specularly reflected rays 53 emanate at the same angle. They are collected by the end of a fiberoptic bundle 54. Diffusely reflected rays 55 are similarly collected by a second fiberoptic bundle 56. An optical filter 57 serves the purpose of a protective window, while absorbing most ambient light below approximately 900 nm. Light rays 58 from the LED 50 that are reflected back by the front and back surfaces of the filter 57 are collected by a third fiberoptic bundle 59. The purpose of this arrangement is to provide a reference channel that monitors the LED 50 intensity. This measurement is used to normalize the specular and diffuse measurements in order to provide stable measurements that are insensitive to fluctuations in LED 50 output. No additional optics are used in front of the fiberoptic bundles 54, 56 and 59, simplifying manufacture of the sensor, and helping to minimize its size.

The three fiberoptics cables 54, 56 and 59, as well as the wires 60 used to provide power to the LED 50, are placed in a protective conduit 61. This conduit connects the above-described optical head 62 to the remainder of the system. The optical head 62 is the only portion of te sensor that must be near the ink form roller 26. It needs to be quite small for installation on a variety of printing presses. The conduit 61 brings the LED wires 60 to a power supply 63, and the fiberoptic cables 54, 56 and 59 to silicon photodiodes 64. These photodiodes 64 convert the optical signals to electrical signals, which are then amplified by amplifiers 65. The amplified signals pass thru filter networks 66 and are multiplexed by a multiplexer 67 prior to conversion to digital form by an A/D converter 68. The A/D converter 68 provides sequentially, the outputs of the specular, diffuse and reference channels. These data are then processed in a computer 69, which normalizes the specular and diffuse channels by the reference channel, and further interprets the data in order to determine ink-water balance. This processed data is either displayed for use by a press operator, or transferred to a control circuit 70 for control of the dampening system.

In order to make the operation of the sensor less sensitive to any ambient light that is transmitted by the optical filter 57, the LED 50 may be pulsed by the power supply 63. The signals output by the amplifiers 65 are then high-pass filtered to remove frequencies associated with ambient light, then rectified and low-pass filtered to provide a smooth output. These filtering operations are carried out by analog circuitry the filter networks 66.

Figure 5:
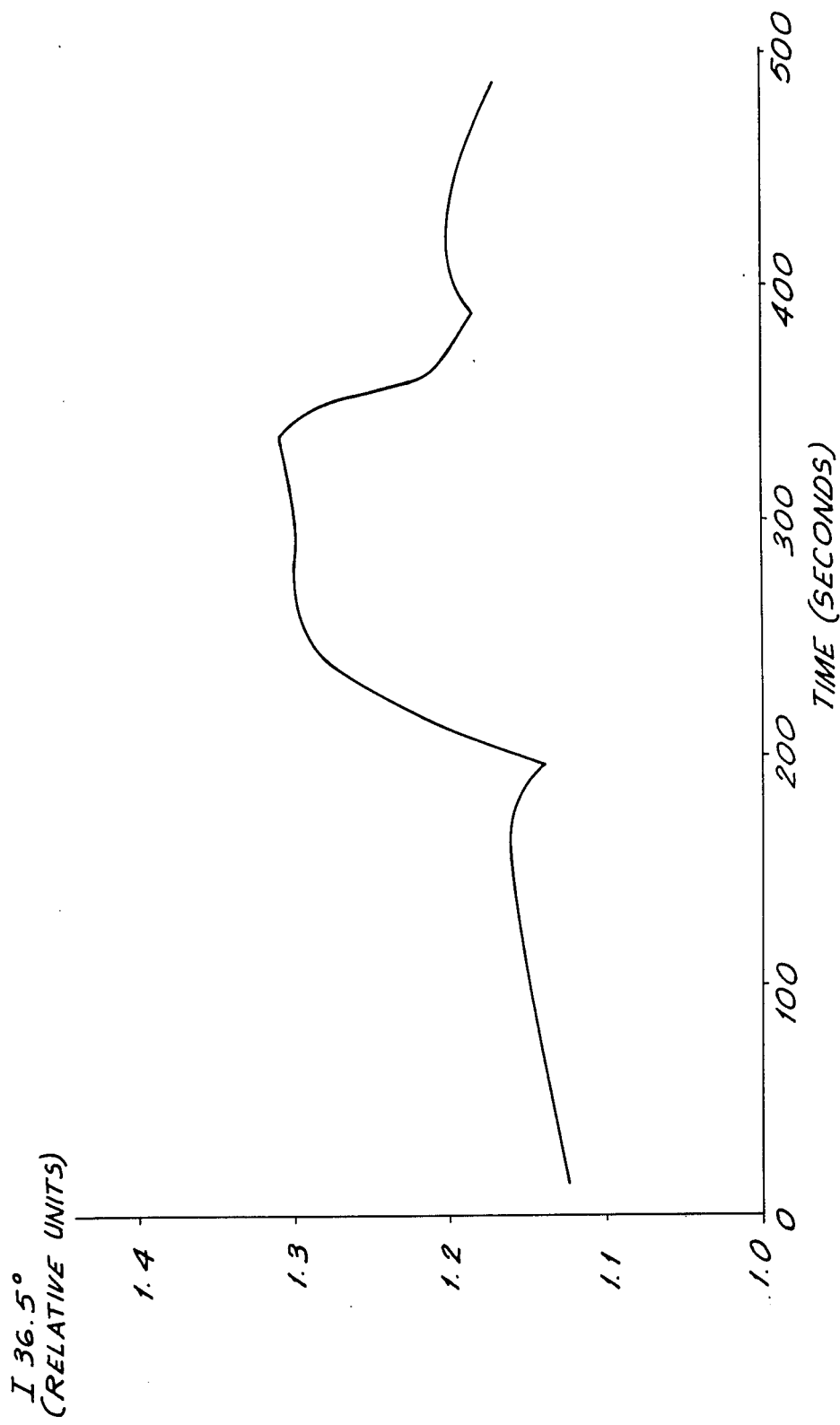
FIG. 5 shows, in graphical form, the typical information provided by the ink-water sensor as the result of on-press measurement.

Use of the sensor on-press is demonstrated by tests conducted on a Commercial 4-color 2 sided web offset press with a Dahlgren dampening system. The sensor was mounted on the last ink form roller, point "P" in FIG. 2, of the upper cyan printing unit. Upon completion of makeready, the press run was continued for 20 minutes before the water level was increased. The water level is controlled by the speed at which the dampening system feeds water to the ink form roller. In this case the speed was increased from 40% to 50% of full speed and maintained at this level for 3 minutes, at which time the speed was returned to 40%. The output of a diffuse channel, located 36.5° from the specular angle is shown in FIG. 5. We see that the change in sensor response is large and immediate for both the increase and decrease in dampening speed, indicating that the state of the emulsion is also immediately affected. The increase in diffusely reflected light at this angle implies that more water is emulsified in the ink.

It should be noted that the invention can be used to analyze emulsions other than those consisting of printing ink and dampening solution. Oil-in-water emulsions, such as salad dressings and dairy products, are two such examples.

While the invention has been described in terms of its preferred embodiments, the words used are words of description rather than limitation and other embodiments of the invention may be emcompassed within the scope of the appended claims.

What is claimed is:

1. A method of measuring, independently, the contents of an emulsion having an oleophilic substance and an hydrophilic substance, wherein one substance is emulsified in and lies on the surface of the other substance, comprising the steps of:
   illuminating the hydrophilic and oleophilic substances with a source of light;
   collecting light reflected by the hydrophilic and oleophilic substances at two or more angles;
   converting the collected light into two or more electrical signals; and
   interpreting the electrical signals to obtain a percentage of one substance emulsified in the other substance, and the amount of one substance lying on the surface of the other substance.

2. A method, as recited in claim 1, in which one of the angles corresponds to the angle of specular reflection of the illumination.

3. A method, as recited in claim 1, wherein the oleophilic substance is printing ink and the hydrophilic substance is lithographic fountain solution.

4. A method as recited in claim 3 in which the collected light is confined to a spectral region in which the absorption coefficients of the ink and the fountain solution are both less than 2000/cm.

5. A method, as recited in claim 3, in which the collected light is confined to a spectral region from 0.9 to 1.0 microns.

6. A method, as recited in claim 3, in which said source of light is a light emitting diode.

7. A method, as recited in claim 3, wherein measurements are made at two angles, one angle corresponding to the angle of specular reflection of the illumination and the other angle corresponding to a nonspecular reflection of the illumination, and in which said source of light is a light emitting diode.

8. A method as recited in claim 7, wherein the printing ink and fountain solution are located on the surface of an ink form roller and one of the angles corresponds to the angle of specular reflection of the illumination.

9. A method, as recited in claim 8, wherein the portion of the ink form roller at which the measurement is made has, just previous to the measurement, contacted a printing plate, and has not yet contacted an ink distributor roller.

10. A method, as recited in claim 9, wherein two measurements are made in sequence, one such measurement being made on a portion of the ink form roller that has previously contacted an image area of the plate, and the other measurement being made on a portion of the ink form roller that has previously contacted a nonimage area of the plate.

11. A method, as recited in claim 9, wherein the measurement is made on a portion of the ink form roller that has previously contacted a nonimage area of the plate.

12. A method, as recited in claim 10, wherein the times at which measurements are made are in synchronism with the rotation of a plate cylinder.

13. A method, as recited in claim 11, wherein the times at which measurements are made are in synchronism with the rotation of a plate cylinder.

14. A method of measuring, independently, the contents of an emulsion having an oleophilic substance and an hydrophilic substance, wherein one substance is emulsified in and lies on the surface of the other substance, comprising the steps of:
   illuminating the surface of the oleophilic and hydrophilic substances with a source of light;
   collecting light reflected by the oleophilic and hydrophilic substances at a first angle relative to the normal to the surface;
   collecting light reflected by the oleophilic and hydrophilic substances at a second angle relative to the normal to the surface;
   collecting light reflected by the oleophilic and hydrophilic substances at a third angle relative to the normal to the surface;
   converting the light collected at the first angle relative to the normal to the surface into a first electrical signal;
   converting the light collected at the second angle relative to the normal to the surface into a second electrical signal;
   converting the light collected at the third angle relative to the normal to the surface into a third electrical signal; and
   interpreting the first, second and third electrical signals to obtain a percentage of one substance emulsified in the other substance, and the amount of one substance lying on the surface of the other substance.

15. A method, as recited in claim 14 in which the first angle corresponds to the angle of specular reflection of the illumination.

16. A method according to claim 14 wherein the oleophilic substance is printing ink and the hydrophilic substance is lithographic fountain solution.

17. A method as recited in claim 16 in which the absorption coefficients of the ink and the fountain solution are both less than 2000/cm.

18. A method, as recited in claim 16, in which the collected light is confined to a spectral region from 0.9 to 1.0 microns.

19. A method, as recited in claim 16, in which said source of light is a light emitting diode.

20. A method as recited in claims 3 or 16 in which one of the angles corresponds to the angle of specular reflection of the illumination.

21. A method, as recited in claim 20, wherein the printing ink and fountain solution are located on the surface of an ink form roller.

22. A method, as recited in claim 21, wherein the portion of the ink form roller at which the measurement is made has, just previous to the measurement, contacted a printing plate, and has not yet contacted an ink distributor roller.

23. A method, as recited in claim 22, wherein two measurements are made in sequence, one such measurement being made on a portion of the ink form roller that has previously contacted an image area of the plate, and the other measurement being made on a portion of the ink form roller that has previously contacted a nonimage area of the plate.

24. A method, as recited in claim 22, wherein the measurement is made on a portion of the ink form roller that has previously contacted a nonimage area of the plate.

25. A method, as recited in claim 23, wherein the times at which measurements are made are in synchronism with the rotation of a plate cylinder.

26. A method, as recited in claim 24, wherein the times at which measurements are made are in synchronism with the rotation of a plate cylinder.

27. Method, as recited in claim 20, wherein the printing ink and fountain solution are located on the surface of a printing plate.

28. Method, as recited in claim 20, wherein the amounts of fountain solution emulsified in and lying on the surface of the ink are controlled by varying the flow of fountain solution and at least one chemical property of the fountain solution.

29. Method, as recited in claim 20, wherein the amounts of fountain solution emulsified in and lying on the surface of the ink are controlled by varying the flow of fountain solution and at least one chemical property of the ink.

30. Method, as recited in claim 21, wherein two measurements are made at different times during the same revolution of said ink form roller for the purpose of measuring the change in time of the amount of fountain solution emulsified in and lying on the surface of the ink.

31. A method of measuring the contents of an emulsion having hydrophilic and oleophilic substances comprising the steps of:
    illuminating the surface of the hydrophilic and oleophilic substances with a source of light;
    collecting light reflected by the hydrophilic and oleophilic substances at a first angle;
    converting the collected light into an electrical signal;
    interpreting the electrical signal to obtain a percentage of the oleophilic and hydrophilic substances in the emulsion.

32. A method, as recited in claim 31, in which the angle corresponds to the angle of specular reflection of the illumination.

33. A method according to claim 31 wherein the oleophilic substance is printing ink and the hydrophilic substance is lithographic fountain solution.

34. A method as recited in claim 33 in which the collected light is confined to a spectral region in which the absorption coefficients of the ink and the fountain solution are both less than 2000/cm.

35. A method, as recited in claim 33, in which the collected light is confined to a spectral region from 0.9 to 1.0 microns.

36. A method, as recited in claim 33, in which said source of light is a light emitting diode.

37. An apparatus for measuring, independently, the amount of hydrophilic substance emulsified in and lying on the surface of an oleophilic substance, comprising:
    light emitting diode for illuminating the two substances;
    a first optical system for collecting light reflected from the two substances substantially at the specular angle;
    a second optical system for collecting light reflected from the two substances at a first nonspecular angle;
    first and second photodetectors for converting the light collected from said first and second optical systems, respectively, into first and second electrical signals, respectively; and
    computing means for interpreting said first, and second electrical signals to obtain a percentage of said hydrophilic substance emulsified in said oleophilic substance, and the amount of said hydrophilic substance lying on the surface of said oleophilic substance.

38. An apparatus, as recited in claim 37, in which said oleophilic substance is printing ink and said hydrophilic substance is lithographic fountain solution.

39. Apparatus, as recited in claim 38, wherein the printing ink and fountain solution to be measured are located on the surface of an ink form roller.

40. Apparatus, as recited in claim 38, wherein the printing ink and fountain solution are located on the surface of a printing plate.

41. Apparatus, as recited in claim 39, wherein two measurements are made in sequence, one such measurement being made on a portion of the ink form roller that has previously contacted an image area of the plate, but not yet contacted an ink distributor roller, and the other measurement being made on a portion of the ink form roller that has previously contacted a nonimage area of the plate, but not yet contacted an ink distributor roller.

42. Apparatus, as recited in claim 38 including circuit means which further includes means for amplifying and filtering the output of said light detecting means.

43. Apparatus, as recited in claim 40, including circuit means which further includes means for amplifying and filtering the output of said light detecting means.

44. An apparatus according to claim 42, wherein the computing means processes the amplified and filtered output of the light detecting means.

45. An apparatus according to claim 43, wherein the computing means processes the amplified and filtered output of the light detecting means.

46. An apparatus according to claim 42, wherein the circuit means further includes a control circuit responsive to the computing means for automatically adjusting the flow of fountain solution.

47. An apparatus according to claim 43, wherein the circuit means further includes a control circuit responsive to the computing means for automatically adjusting the flow of fountain solution.

48. An apparatus for measuring the amount of a hydrophilic substance emulsified in an oleophilic substance, comprising:
    a source of light for irradiating the two substances;
    first means for detecting light specularly reflected from the two substances;
    second means for detecting light nonspecularly reflected from the two substances; and
    circuit means responsive to said first and second light detecting means for providing an indication of the percentage of hydrophilic substance emulsified in the oleophilic substance.

49. An apparatus according to claim 48 which further includes third light detecting means for detecting light nonspecularly reflected from the two substances.

50. An apparatus according to claim 49 wherein the oleophilic substance is printing ink and the hydrophilic substance is lithographic fountain solution.

51. Apparatus, as recited in claim 50, wherein the printing ink and fountain solution to be measured are located on the surface of an ink form roller.

52. Apparatus, as recited in claim 50, wherein the printing ink and fountain solution are located on the surface of a printing plate.

53. Apparatus, as recited in claim 51, wherein two measurements are made in sequence, one such measurement being made on a portion of the ink form roller that has previously contacted an image area of a plate, but not yet contacted an ink distribution roller, and the other measurement being made on a portion of the ink form roller that has previously contacted a nonimage area of the plate, but not yet contacted an ink distribution roller.

54. Apparatus, as recited in claim 52, including circuit means which further includes means for amplifying and filtering the output of said light detecting means.

55. Apparatus, as recited in claim 50, wherein said circuit means further includes means for amplifying and filtering the output of said light detecting means.

56. An apparatus according to claim 54, wherein said circuit means further includes computing means for processing the amplified and filtered output of said light detecting means.

57. An apparatus according to claim 55, wherein said circuit means further includs computing means for processing the amplified and filtered output of said light detecting means.

58. An apparatus according to claim 56, wherein the circuit means further includes a control circuit responsive to the computing means for automatically adjusting the flow of fountain solution.

59. An apparatus according to claim 57, wherein the circuit means further includes a control circuit responsive to the computing means for automatically adjusting the flow of fountain solution.

60. An apparatus according to claim 49 wherein said first light detecting means is disposed at an angle differing from said second light detecting means by at least 5° and said third light detecting means is disposed at an angle differing from said first and second slight detecting means by at least 5°.

61. An apparatus according to claim 59 wherein said first light detecting means is disposed at an angle differing from said second light detecting means by at least 5° and said third light detecting means is disposed at an angle differing from said first and second light detecting means by at least 5°.

62. An apparatus according to claim 48 wherein said light detecting means including a plurality of fiber optic cables.

63. An apparatus according to claim 61 wherein said light detecting means includes a plurality of fiber optic cables.

* * * * *